United States Patent [19]

Stirnadel

[11] Plant 4,931

[45] Nov. 9, 1982

[54] EUPHORBIA HYBRID "SULEIKA"

[76] Inventor: Alfred Stirnadel, Schwarzwaldstr. 80, 6660 Zweibrucken 15, Fed. Rep. of Germany

[21] Appl. No.: 245,909

[22] Filed: Mar. 20, 1981

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Synnestvedt & Lechner

[57] ABSTRACT

This invention relates to a Euphorbia hybrid characterized by limited vertical growth and large blossoms.

1 Drawing Figure

This invention relates to a new Euphorbia hybrid to be known as "Suleika" and characterized by limited vertical growth and large blossom size. "Suleika" was created in the course of breeding studies on the Euphorbia hybrid "Gabriela". The new variety belongs to the *Euphorbia milii* group.

The new variety resulted from selective inbreeding by manual fertilization (endogamic hybridization—i.e., pollen of the same blossom on its own stigma) of the Euphorbia hybrid "Gabriela" conducted in 1974 and the parents are therefore Euphorbia "Gabriela". After manual fertilization, the seeds were harvested and sown. The seedlings were observed until they blossomed and a positive selection made on the basis of results in 1975. "Suleika", which is the subject of this application, was considered the most beautiful and best in growth, structure, blossom size and profusion of blossoms. "Suleika" is uniform, stable and has been and can be reproduced fully at any time through vegetative propagation.

One of the most important new characteristics of "Suleika" is the bringing forth of blossoms at the germinating tip and, at the same time, in the upper leaf axes and the vertical growth of the plant is thereby limited. Another is the size of the blossoms (cyathia)—they are significantly larger than blossoms of the parent variety "Gabriela".

The individual characteristics of the new Euphorbia variety "Suleika" and some comparisons with its parent "Gabriela" are summarized below; and in the following description, the color identifications preceeded by the initials "RHS-" refer to Royal Horticultural Society Colour Chart color designations:

p *Plant.*—The "Suleika" variety grows in an upright habit and liits its growth vertically to a height of about b 10 to 12 cm by bringing forth blossom clusters from te upper leaf axes at heights of 6–12 cm and also at the germinating tip. In contrast, the parent "Gabriela", develops blossoms at heights from 10 cm and upward and the plant keeps on growing.

As in all plants of this species, "Suleika" exudes a white milky sap when subjected to injury.

*Stem.*—The "Suleika" stem is slightly succulent, about 8–12 mm in diameter, green in color, turning grey-brown with age. The parent plant has a somewhat larger (10–15 mm) grey-green stem.

The "Suleika" stems have 4 or 5 barely discernable ridges, nodes are formed on the ridges at 1.5 to 2 cm intervals and fanning, comb-like rows of up to 6 smooth thorns of irregular size at each node; when highly developed, the thorns are soft, red-brown in color and up to 8 mm in length. In contrast, "Gabriela" develops a vertical row of up to 10 thorns on each node, of varying size, irregular, up to 20 mm in length, grey and hard.

*Leaves.*—The "Suleika" leaves are obvate with a short stalk, substantially the same shape but somewhat smaller than those of the parent "Gabriela". The "Suleika's" leaves are alternately arranged, slightly pulpy, green on the upper side and light green on the underside; leaves of a young "Suleika" plant are leaves grow up to about 6–8 cm in length (vs. 8–12 cm in "Gabriela") and about 3 cm in width. Unlike the "Gabriela", the longitudinal edges of the "Suleika" plant show a slight upward curving along the middle vein.

*Blossom cluster.*—"The Suleika" exhibits a compact blossom cluster and does not bloom continuously. The parent "Gabriela" gives a dispersed appearance and is continuously in bloom.

*Pedicel.*—"Suleika" plants have light green, non-glutinous pedicels, of varied length—usually about 4–9 cm in length up to the first ramification and about 3–4 mm in thickness. "Suleika" blossom clusters form at the germinating tip and upper leaf axes, when seen from above in a state of bloom, the blossom clusters are almost on one level. The pedicels of the "Gabriela" are green, reddish with much sun, slightly glutinous and of from about 8 to 15 cm in length up to the first ramification, the length will vary depending on conditions for growth and age of the plant.

*Cyathia.*—Each blossom cluster of the "Suleika" is of layered configuration since two new blossoms develop from each individual blossom (diaxial ramification) and depending on the health of the plant and the environment from 3–6 tiers can simultaneously develop one upon another; single blossoms include two salmon-red (RHS-50B on the upper side and RHS-52C on the under side) bracts surrounding the flower organs. The bracts are veined, round, slightly superposed and of a diameter of about 1.5 to 3 cm. The actual blossom is dull yellowish and the three-part female hilium appears during the sapling stage—i.e., the time from the closed flower bud to the opening of the bracts (false blossom) and the subsequent appearance of the female ovary (sexual maturity)—disappears again after 2–3 days of exposure to weather and is covered by the male stamen which grows up to 4 mm in height. This period of time relates to the single blossom only and not to a blossom cluster or to the plant. The topmost blossoms, from the fifth tier, have a diameter of about 1.5 to 2 cm. Where an abundance of blossoms have been formed, the individual bracts in the lower tiers have a diameter of about 3 cm.

In contrast with "Suleika", the bracts of "Gabriela" are carmine red (RHS-52A upper side and RHS-52C under side, and with much sun intense red); with the growth and formation of a new leaf, a bud appears in each new shoot and gradually unfolds. In a favorable environment, the "Gabriela" plant blooms uninterruptedly, and optimally, it has about 6–8 pedicels on each of which a tiered blossom cluster developing up to 32 single blossoms (each having two bracts).

After the "Suleika" has fully brought forth its blossom cluster, with 4 or 5 tiers of bracts, it produces at the base several sideshoots, which can be used as slip material. Generally, the blossom clusters are removed from the mother plants. As in the case of all other Euphorbia slips, after being cut the slips are dipped in lukewarm water, in order to stop the milk sap exuding, and are subsequently put in propagation substratum; with high humidity and a temperature of at least 20° C., roots sprout in approximately 8–10 days.

The enclosed color photographs show the plant of the new Euphorbia variety in full bloom.

I claim:

1. A new stable and distinct Euphorbia hybrid resulting from selective inbreeding pollination ex "Gabriela" substantially as herein shown and described, and characterized in that blossom clusters develop only at the germinating tip and upper leaf axes thereby limiting vertical growth to a height of about 10–12 cm.

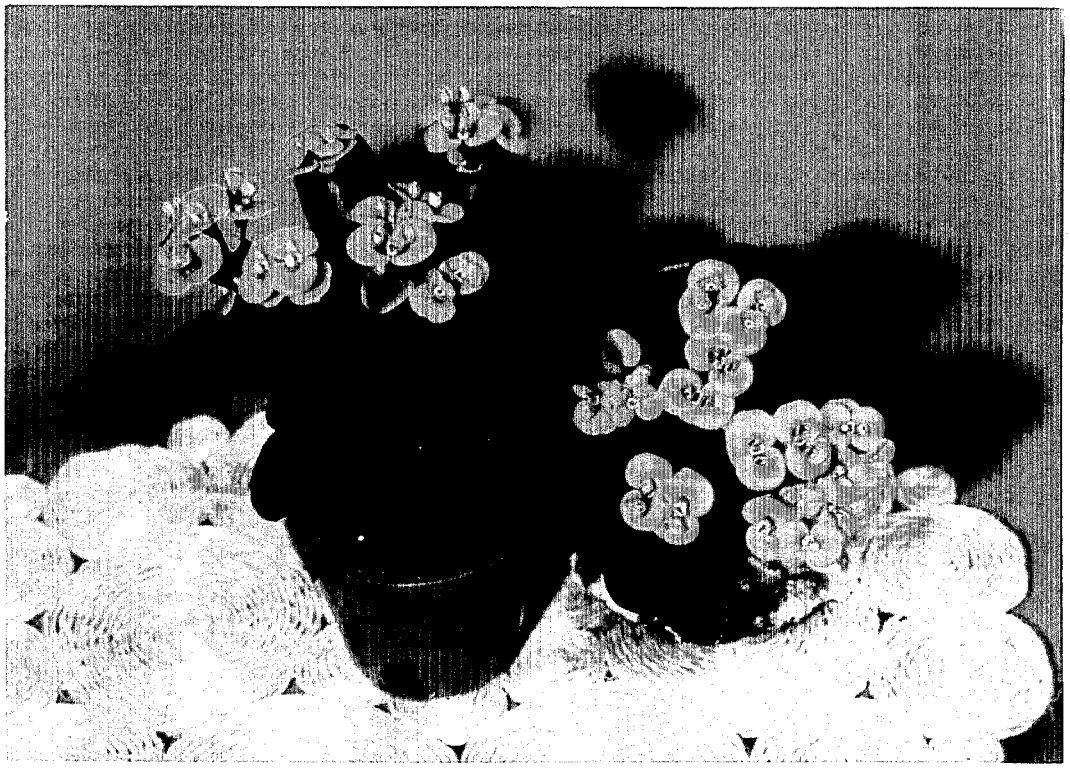

* * * * *